US011911358B2

(12) United States Patent
Streeper et al.

(10) Patent No.: US 11,911,358 B2
(45) Date of Patent: Feb. 27, 2024

(54) DICARBOXYLIC ACID ESTERS FOR INDUCING AN ANALGESIC EFFECT

(71) Applicant: NEW FRONTIER LABS, LLC, San Antonio, TX (US)

(72) Inventors: Robert T. Streeper, San Antonio, TX (US); Elzbieta Izbicka, San Antonio, TX (US)

(73) Assignee: NEW FRONTIER LABS, LLC

( * ) Notice: Subject to any disclaimer, the term of this patent is extended or adjusted under 35 U.S.C. 154(b) by 0 days.

(21) Appl. No.: 17/552,943

(22) Filed: Dec. 16, 2021

(65) Prior Publication Data
US 2022/0184023 A1 Jun. 16, 2022

Related U.S. Application Data

(60) Provisional application No. 63/126,387, filed on Dec. 16, 2020.

(51) Int. Cl.
| | | |
|---|---|---|
| *A61K 31/23* | (2006.01) | |
| *A61P 29/02* | (2006.01) | |
| *A61K 9/00* | (2006.01) | |

(52) U.S. Cl.
CPC .......... *A61K 31/23* (2013.01); *A61K 9/0014* (2013.01); *A61P 29/02* (2018.01)

(58) Field of Classification Search
CPC .... A61K 31/23; A61K 31/225; A61K 9/0019; A61K 9/0053; A61K 2300/00; A61K 31/337; A61K 31/573; A61K 45/06; A61K 9/0014; A61P 43/00; A61P 3/10; A61P 3/08; A61P 17/10; A61P 25/00; A61P 29/00; A61P 3/00; A61P 31/04; A61P 31/12; A61P 35/00; A61P 37/02; A61P 9/10; A61P 29/02; A61P 3/06; A61P 39/02; Y02A 50/30
See application file for complete search history.

(56) References Cited

U.S. PATENT DOCUMENTS

| | | | |
|---|---|---|---|
| 2009/0326017 A1 | 12/2009 | Smith | |
| 2014/0094516 A1* | 4/2014 | Streeper | A61P 31/12 |
| | | | 435/375 |

FOREIGN PATENT DOCUMENTS

| | | |
|---|---|---|
| CN | 111544381 A | 8/2020 |
| WO | 2013/158541 A1 | 10/2013 |

OTHER PUBLICATIONS

Velazquz et al. (Pharmacological Research 55 (2007) 578-589.) (Year: 2007).*
Paschou et al., "Pain management of chronic wounds: Diabetic ulcers and beyond", Maturitas, 2018, pp. 17-21, vol. 117.
Thurlow et al., "Lack of nutritional immunity in diabetic skin infections promotes *Staphylococcus aureus* virulence", Sci. Adv., Nov. 13, 2020, pp. 1-11, vol. 6, eabc5569.
Al-Marabeh et al., "A prodrug approach to enhance azelaic acid percutaneous availability", Pharmaceutical Development and Technology, Jun. 27, 2016, pp. 1-10.

(Continued)

*Primary Examiner* — Savitha M Rao
(74) *Attorney, Agent, or Firm* — Pillsbury Winthrop Shaw Pittman LLP (CV)

(57) ABSTRACT

The disclosure provides compositions and methods of inducing an analgesic effect. In particular, the methods include administering to a subject in need a pharmaceutical composition comprising a dicarboxylic acid ester.

11 Claims, 3 Drawing Sheets

Modulation of ATP release by pattern recognition receptor agonists alone and in the presence of diethyl azelate in human plasmacytoid dendritic cells

(56) References Cited

OTHER PUBLICATIONS

Von Aulock et al., "GCSF: Boosting endogenous production—a new strategy?", Current Opinion in Investigational Drugs, 2004, pp. 1148-1152, vol. 5(11).
Backstrom et al., "Induction of Experimental Arthritis in BalbC Mice by Inclusion of a Foreign Protein in the Collagen Inoculum", Scandinavian Jornal of Immunology, 2008, pp. 322-328, vol. 67.
Balkrishna et al., "Anti-Inflammatory and Anti-Arthritic Efficacies of an Indian Traditional Herbo-Mineral Medicine "Divya Amvatari Ras" in Collagen Antibody-Induced Arthritis (CAIA) Mouse Model Through Modulation of IL-6/IL-1β/TNF-α/NFκB Signaling", Frontiers in Pharmacology, Jul. 1, 2019, pp. 1-19, vol. 10, Article 659.
Basbaum et al., "Cellular and Molecular Mechanisms of Pain", Cell, Oct. 16, 2009, pp. 267-284, vol. 139(2).
Beetge et al., "The influence of the physicochemical characteristics and pharmacokinetic properties of selected NSAID's on their transdermal absorption", Department of Pharmaceutics, 2000, pp. 261-264, vol. 193.
Bost et al., "Induction of Colony-Stimulating Factor Expression following *Staphylococcus* or *Salmonella* Interaction with Mouse or Human Osteoblasts", Infection and Immunity, Sep. 2000, pp. 5075-5083, vol. 68(9).
Caplazi et al., "Mouse Models of Rheumatoid Arthritis", Veterinary Pathology, 2015, pp. 819-826, vol. 52(5).
Chao et al., "Early Systemic Granulocyte-Colony Stimulating Factor Treatment Attenuates Neuropathic Pain after Peripheral Nerve Injury", Plos One, Aug. 24, 2012, pp. 1-13, vol. 7(8), e43680.
Conus et al., "Leptin is an eosinophil survival factor", Journal of Allergy and Clinical Immunology, Oct. 24, 2005, pp. 1228-1234, vol. 116(6).
Deuis et al., "Methods Used to Evaluate Pain Behaviors in Rodents", Frontiers in Molecular Neuroscience, Sep. 6, 2017, pp. 1-17, vol. 10, Article 284.
Ferrari et al., "Plasma Membrane Mechanisms in a Preclinical Rat Model of Chronic Pain", The Journal of Pain, Jan. 2015, pp. 60-66, vol. 16(1).
Grace et al., "Harnessing pain heterogeneity and RNA transcriptome to identify blood-based pain biomarkers: a novel correlational study design and bioinformatics approach in a graded chronic constriction injury model", Journal of Neurochemistry, Sep. 2012, pp. 976-994, vol. 122(5).
Greisen et al., "Acute Pain Induces Insulin Resistance in Humans", Anesthesiology, Sep. 2001, pp. 548-584, vol. 95(3).
Gurven et al., "Rapidly declining body temperature in a tropical human population", Sci. Adv., Oct. 28, 2020, pp. 1-8, vol. 6.
Hareng et al., "Induction and Regulation of Endogenous Granulocyte Colony-Stimulating Factor Formation", Biol. Chem., Oct. 2002, pp. 1501-1517, vol. 383.
Holmdahl et al., "Homologous Type II Collagen Induces Chronic and Progressive Arthritis in Mice", Arthritis and Rheumatism, Jan. 1986, pp. 106-113, vol. 29(1).
Homayun et al., "Challenges and Recent Progress in Oral Drug Delivery Systems for Biopharmaceuticals", Pharmaceutics, 2019, pp. 1-29, vol. 11(129).
Hunskaar et al., "Antinociceptive Effects of Orphenadrine Citrate in Mice", European Journal of Pharmacology, 1985, pp. 221-226, vol. 111.
Hunskaar et al., "A Modified Hot-Plate Test Sensitive to Mild Analgesics", Behavioural Brain Research, 1986, pp. 101-108, vol. 21.
Kandalla et al., "M-CSF improves protection against bacterial and fungal infections after hematopoietic stem/ progenitor cell transplantation", Journal of Experimental Medicine, 2016, pp. 2269-2279, vol. 213(11).
Kinfe et al., "Leptin and Associated Mediators of Immunometabolic Signaling: Novel Molecular Outcome Measures for Neurostimulation to Treat Chronic Pain", International Journal of Molecular Sciences, Sep. 24, 2019, pp. 1-15, vol. 20(4737).
Krock et al., "Pain pathogenesis in rheumatoid arthritis—what have we learned from animal models", Department of Physiology and Pharmacology, Centre for Molecular Medicine, Karolinska Institutet, Stockholm, Sweden, 2018, pp. 1-33.
Kumar et al., "Definition of pain and classification of pain disorders", Journal of Advanced Clinical & Research Insights, 2016, pp. 87-90, vol. 3(3).
Lacagnina et al., "Toll-like receptors and their role in persistent pain", Pharmacol Ther., Apr. 1, 2018, pp. 145-158, vol. 184.
Laird et al., "The Systemic Inflammatory Response and Its Relationship to Pain and Other Symptoms in Advanced Cancer", The Oncologist, 2013, pp. 1050-1055, vol. 18.
Li et al., "Intrathecal leptin inhibits expression of the P2X2/3 receptors and alleviates neuropathic pain induced by chronic constriction sciatic nerve injury", Molecular Pain, 2013, pp. 1-9, vol. 9(65).
Liao et al., "An early granulocyte colony-stimulating factor treatment attenuates neuropathic pain through activation of mu opioid receptors on the injured nerve", Scientific Reports, May 16, 2016, pp. 1-10.
Liu et al., "Emerging role of Toll-like receptors in the control of pain and itch", Neurosci Bull, Apr. 1, 2012, pp. 131-144, vol. 28(2).
Lu et al., "Rapid S-nitrosylation of actin by NO-generating donors and in inflammatory pain model mice", Molecular Pain, 2011, pp. 1-13, vol. 7(101).
Marino et al., "Structural analysis of cysteine S-nitrosylation: a modified acid-based motif and the emerging role of trans-nitrosylation", J Mol Biol., Jan. 29, 2010, pp. 844-859, vol. 395(4).
Metcalf, "The CSFs and Cancer", Nat Rev Cancer, Jun. 2010, pp. 425-434, vol. 10(6).
Olama et al., "Synovial/Serum leptin ratio in rheumatoid arthritis: the association with activity and erosion", Rheumatol. Int., 2012, pp. 683-690, vol. 32., published online Dec. 8, 2010.
Omoigui, "The Biochemical Origin of Pain: The origin of all Pain is Inflammation and the Inflammatory Response. Part 2 of 3—Inflammatory Profile of Pain Syndromes", Med Hypotheses, 2007, pp. 1169-1178, vol. 69(6).
Reed et al., "GM-CSF action in the CNS decreases food intake and body wieght", Journal of Clinical Investigation, Nov. 2005, pp. 3035-3044, vol. 115(11).
Schaible et al., "Update on peripheral mechanisms of pain: beyond prostaglandins and cytokines", Arthritis Research & Therapy, 2011, pp. 1-8. vol. 13(210).
Sharma et al., "Leptin, IL-10 and Inflammatory Markers (TNF-a, IL-6 and IL-8) in Pre-Eclamptic, Normotensive Pregnant and Healthy Non-Pregnant Women", American Journal of Reproductive Immunology, 2007, pp. 21-30, vol. 58.
Stosser et al., "Hematopoietic colony-stimulating factors: new players in tumor—nerve interactions", J. Mol. Med., 2011, ePublished Nov. 16, 2010, pp. 321-321, vol. 89.
Tewari et al., "Granulocyte-Macrophage Colony Stimulating Factor as an Indirect Mediator of Nociceptor Activation and Pain", J. Neurosci, Mar. 11, 2020, pp. 2189-2199, vol. 40(11).
Thakur et al., "Therapeutic Implications of Toll-like Receptors in Peripheral Neuropathic Pain", Pharmacological Research, Jan. 2017, ePublished Nov. 25, 2016, pp. 1-26.
Tian et al., "Emerging role of leptin in rheumatoid arthritis", Clinical & Experimental Immunology, 2014, pp. 557-570, vol. 177.
Treede et al., "A classification of chronic pain for ICD-11", Pain, www.painjournalonline.com, Jun. 2015, pp. 1003-1007, vol. 156(6).
Wahlen et al., "Plasma Protein Pattern Correlates With Pain Intensity and Psychological Distress in Women With Chronic Widespread Pain", Frontiers in Psychology, Nov. 29, 2018, pp. 1-19, vol. 9, Article 2400.
Younger et al., "Association of Leptin with Body Pain in Women", Journal of Women's Health, 2016, pp. 252-760, vol. 25(7).
Zaid et al., "Arthritogenic alphaviruses: epidemiological and clinical perspective on emerging arboviruses", www.thelancet.com/infection, published online Nov. 2, 2020. pp. 1-11.
Zhai et al., "A Correlative Relationship Between Chronic Pain and Insulin Resistance in Zucker Fatty Rats: Role of Downregulation of Insulin Receptors", The Journal of Pain, Apr. 2016, pp. 404-413, vol. 17(4).

(56) References Cited

OTHER PUBLICATIONS

Zhang et al., "Cytokines, Inflammation and Pain", Int. Anesthesiol. Clin., 2007, pp. 27-37, vol. 45(2).

Filippis et al., "Adelmidrol, a palmitoylethanolamide analogue, reduces chronic inflammation in a carrageenin-granuloma model in rats", J. Cell. Mol. Med., 2009, pp. 1086-1095, vol. 13(6).

D'Amico et al., "ALIAmides Update: Palmitoylethanolamide and Its Formulations on Management of Peripheral Neuropathic Pain", International Journal of Molecular Sciences, 2020, pp. 1-27.

Izbecka et al., "Adaptive Membrane Fluidity Modulation: A Feedback Regulated Homeostatic System and Target for Pharmacological Intervention", In Vivo, Nov. 2021, pp. 3073-3095, vol. 35(6).

\* cited by examiner

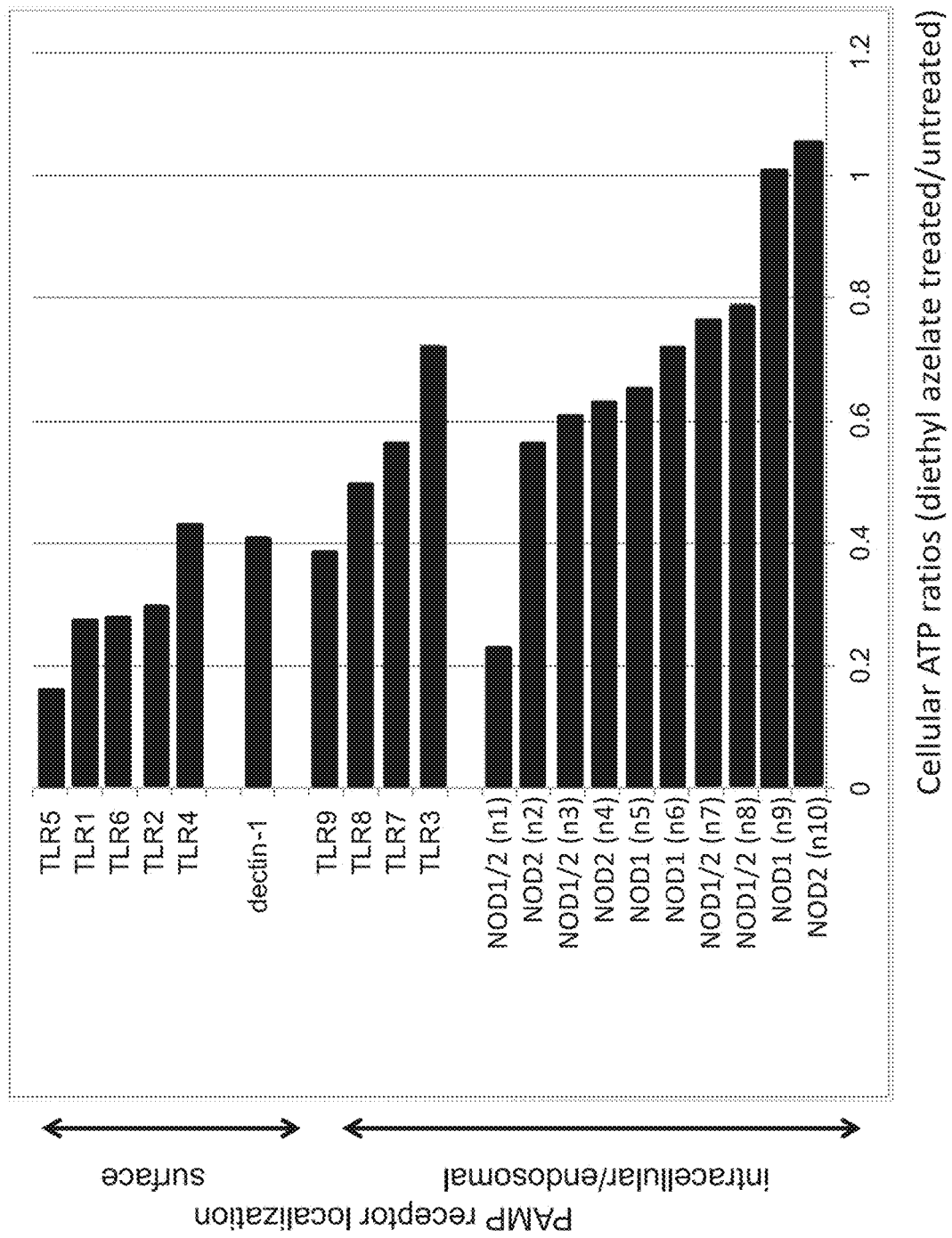
Figure 1. Modulation of ATP release by pattern recognition receptor agonists alone and in the presence of diethyl azelate in human plasmacytoid dendritic cells

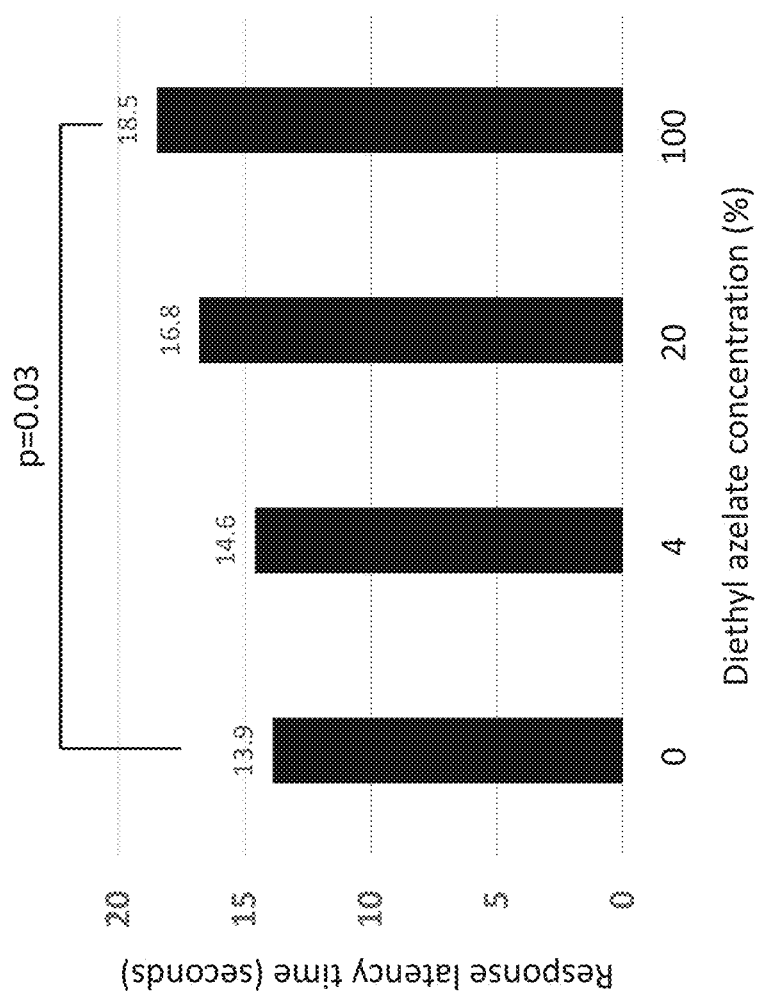
Figure 2. Effect of topical diethyl azelate on response latency in a hot plate test *in vivo*

Figure 3. Diethyl azelate-mediated disruption of cholera toxin binding to plasma membranes of human peripheral blood mononuclear cells

DICARBOXYLIC ACID ESTERS FOR INDUCING AN ANALGESIC EFFECT

RELATED APPLICATIONS

This patent application claims priority to U.S. Provisional Patent Application No. 63/126,387, filed Dec. 16, 2020, entitled "DICARBOXYLIC ACID ESTERS FOR INDUCING AN ANALGESIC EFFECT" naming inventors Robert T. STREEPER and Elzbieta IZBICKA. The entire content of the foregoing patent application is incorporated herein by reference.

FIELD OF THE INVENTION

The disclosure relates to methods and pharmaceutical compositions including dicarboxylic acid esters for inducing an analgesic effect.

INTRODUCTION

Anesthetic and analgesic drugs are widely utilized for the treatment of pain.

Recently, Pavil et al. describe in detail the biochemical mechanisms by which general anesthetics exert their pharmacological effects. Pavil shows that inhalational anesthetics disrupt the ordering of lipid rafts and by dint of this disruption induce anesthesia. The best-studied lipid rafts are membrane domains enriched in cholesterol and sphingomyelin (e.g., monosialotetrahexosylganglioside1 "GM1") that bind cholera toxin B (CTxB). GM1 lipid rafts contain phospholipase D2 (PLD2). Inhalational anesthetics increase the fluidity of, and thereby disrupt, GM1 lipid rafts causing PLD2 to depart the lipid raft and translocate to the proximity of TREK1. Once there, PLD2 hydrolyzes phosphatidylcholine (PC) to produce phosphatidic acid (PA) and choline. The PA then binds to and activates TREK1. When TREK1 is activated the resultant potassium influx induces unconsciousness and analgesia. Pavil et al. also show that PLD2 translocation also activates a second type of channel called TRAAK which is an anesthetic-insensitive homolog of TREK-1. [M. A. Pavel, et al., PNAS, (2020) 117(24):13757-66].

The inventors have discovered that dicarboxylic acid esters of the present disclosure are effective for the relief of pain when applied topically, with the data showing that, in one embodiment, the diethyl azelate (DEA) also increases the fluidity of GM1 lipid rafts and thus prevents the formation of membrane attack complexes by both cholera toxin B subunit (CTxB) and anthrax toxin protective antigen (PA). The inventors thus contend that DEA modulates neurotransmission in a manner similar to inhalational anesthetics. Accordingly, the dicarboxylic acid esters, exemplified by DEA, have analgesic effects similar to the inhalational anesthetics, as they perturb membrane fluidity.

At the most fundamental level all types of pain, other than psychogenic pain, involve the transmission of aversive or noxious stimuli to the central nervous system via the afferent nerves. The nerve impulse transmission that occurs must at multiple points in the chain of signal transmission cross cellular plasma membranes [A. Basbaum, et al., Cell. (2009) 139(2):267-84]. The role of the plasma membrane in the mechanism of pain has been demonstrated in vivo whereby disruption of nerve signaling by increasing lipid raft fluidity via depletion of cholesterol by cyclodextrin reversibly diminished hyperalgesia induced by prostaglandin E2 (PGE2) [Ferrari, L, et al., J. Pain (2015) 16(1):60-6].

The biochemical mediators of pain include cytokines, neuropeptides, lipids, growth factors and neurotransmitters. Additional cellular signals and sensors of interest in pain control include colony stimulating factors (CSFs) and leptin.

Several members of the CSF superfamily play a beneficial role in pain mitigation. Early systemic granulocyte-colony stimulating factor (G-CSF) treatment attenuates neuropathic pain after peripheral nerve injury [P. Chao, et al., PLoS ONE (2012) 7(8):e43680]. G-CSF primes neutrophilic granulocytes for improved host defense and reduces the release of pro-inflammatory cytokines [T. Hartung, et al., Blood. (1995) 85(9):2482-9]. GM-CSF action in the central nervous system decreases food intake and body weight [J. Reed, et al., J. Clin. Invest. (2005) 115(11):3035-44]. However, in the above reports the CSFs were administered exogenously as biologic drugs. Boosting endogenous production of G-CSF has been proposed as a new therapeutic strategy [S. Von Aulock, et al., Curr. Opin. Investig. Drugs (2004) 5(11):1148-52], but heretofore the only known way to induce CSFs is by bacterial or viral antigen stimuli. No small molecule inducers of CSFs, also known as secretagogues, have been identified to date.

Leptin has been shown to alleviate neuropathic pain induced by chronic nerve injury [X. Li, et al., Mol. Pain (2013) 9:65].

The inventors also have demonstrated that dicarboxylic acid esters induce a number of changes in cellular and organismal signaling that are therapeutically useful. In addition to their other pharmacological activities, dicarboxylic acid esters induce the cellular release and/or production of signaling molecules that have analgesic properties. Responsive cellular molecules include leptin, macrophage colony stimulating factor (M-CSF), granulocyte colony stimulating factor (G-CSF), and granulocyte-macrophage colony stimulating factor (GM-CSF). In addition, the inventors have discovered that treatment of mammalian cells and tissues with dicarboxylic acid esters can suppress the production of markers associated with pain, which include inducible nitric oxide synthase (iNOS) [Y. Kwok, et al., PLoS One. 2012; 7(8):e44232], S-nitrosylated cysteine residues in cellular proteins [J. Zhang, et al., Int. Anesthesiol. Clin. (2007) 45(2):27-37], prostaglandin E2 (PGE2) [A. Ahlawat, et al., Eur. J. Pharmacol. (2018) 818:419-28], and adenosine triphosphate (ATP) [Mense, Dtsch Arztebl Int 2008; 105(12):214-9].

SUMMARY OF THE INVENTION

Aspects of the present disclosure provides methods and pharmaceutical compositions including a dicarboxylic acid ester of Formula I: $R_2OOC-(CH_2)_n-COOR_1$, wherein n is between 4 and 10, and each $R_1$ and $R_2$ are independently a lower alkyl, for inducing an analgesic effect in a subject. Certain embodiments herein relate to inducing an analgesic effect in a subject, thereby inhibiting pain due to the activation of pattern recognition receptors (PRR) including Toll-like receptors (TLRs), nucleotide oligomerization domain (NOD) receptors, and/or Dectin receptors.

Certain embodiments herein relate to inducing an analgesic effect, thereby inhibiting a localized pain in a subject, by promoting the secretion of leptin, macrophage colony-stimulating factor (M-CSF), granulocyte macrophage colony-stimulating factor (GM-CSF), and/or granulocyte colony-stimulating factor (G-CSF).

In some aspects, embodiments herein relate to methods and pharmaceutical compositions including a dicarboxylic acid ester of Formula I for inducing an analgesic effect, thereby inhibiting a localized pain in a subject, by suppressing the expression and secretion of prostaglandin E2 (PGE2) and/or inducible nitric oxide synthase (iNOS) and/or adenosine triphosphate (ATP).

In some aspects, embodiments herein relate to methods of inducing an analgesic effect, thereby inhibiting localized pain in a subject, the method including the step of administering to the subject in need a dicarboxylic acid ester of Formula I, wherein administration results in a reduction in a symptom associated with the pain condition.

In some aspects, embodiments herein relate to uses of a dicarboxylic acid ester of Formula I in the manufacture of a medicament for inducing an analgesic effect, thereby inhibiting localized pain in a subject.

In some aspects, embodiments herein relate to uses of a dicarboxylic acid ester of Formula I for inducing an analgesic effect, thereby inhibiting localized pain in a subject.

In some aspects, embodiments herein relate to uses of a dicarboxylic acid ester of Formula I in the manufacture of a medicament for inducing an analgesic effect in a subject, thereby inhibiting localized pain in a subject, such as acute pain, chronic pain, nociceptive pain, neuropathic pain, or nociplastic pain.

In some aspects, embodiments herein relate to uses of a dicarboxylic acid ester of Formula I in the manufacture of a medicament for inducing an analgesic effect in a subject, thereby inhibiting localized pain responsive to the modulation of one or more receptors in a subject in need selected from iNOS, ATP, and pattern recognition receptors (PRR) including Toll Like, NOD and Dectin receptors.

In some aspects, embodiments herein relate to uses of a dicarboxylic acid ester of Formula I in the manufacture of a medicament for inducing an analgesic effect, thereby inhibiting localized pain in a subject, by upregulating the activity and/or expression of one or more of leptin, M-CSF, G-CSF, and GM-CSF, or downregulating the activity and/or expression or release of at least one of ATP, iNOS and PGE2.

DESCRIPTION OF THE DRAWINGS

The following drawings demonstrate certain aspects of the present disclosure. The disclosure may be better understood by reference to one or more of these drawings in combination with the detailed description of specific embodiments presented herein.

FIG. 1 is a bar graph showing the modulation of ATP release by PRR agonists alone and in the presence of diethyl azelate (DEA) in human plasmacytoid dendritic cells according to certain embodiments of the disclosure.

FIG. 2 shows the effect of topical DEA on a hindlimb response latency in a hot plate test in vivo according to certain embodiments of the disclosure.

FIG. 3 shows images of human peripheral blood mononuclear cells co-exposed to fluorescently labeled cholera toxin B subunit without DEA treatment (left column) and with DEA treatment (right column) according to certain embodiments of the disclosure.

DETAILED DESCRIPTION

All applications, publications, patents and other references, cited herein are incorporated by reference in their entirety.

As used herein, the singular forms "a," "an" and "the" include plural referents unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Ranges may be expressed herein as from "about" one particular value, and/or to "about" another particular value. As used herein, the term "about," is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

As used herein, all numerical values or numerical ranges include integers within such ranges and fractions of the values or the integers within ranges unless the context clearly indicates otherwise. In addition, such ranges are also intended to include the numbers themselves and any sub-range between them. This range may be integral or continuous between and including the end values. Thus, for example, reference to a range of about 3 hours to about 10 hours, includes 3 hours, 4 hours, 5 hours, etc., as well as 3 hours and 1 minute, 3 hours and 2 minutes, 3 hours and 4 minutes, etc., 4 hours and 1 minute, 4 hours and 2 minutes, 4 hours and 4 minutes, etc. and so forth. Reference to a range of 90-100% includes 92.2% to 97.5%, 91.5 to 94.5, etc. Reference to a range of 1 to 25 days include sub-ranges from 1 day to 5 days, or from 3 days to 7 days, or from 5 days to 25 days.

As used herein, the term "comprising" is intended to mean that the pharmaceutical compositions (or compositions) and methods include the recited elements, but not excluding others. The term "consisting essentially of," as applied to the compositions of the present embodiments, means the composition can contain additional elements as long as the additional elements do not materially alter the composition. The term "materially altered," as applied to a composition, refers to an increase or decrease in the therapeutic effectiveness of the composition as compared to the effectiveness of a composition consisting of the recited elements. In other words, "consisting essentially of" when used to define compositions, shall mean excluding other components of any essential significance to the composition. Thus, a composition consisting essentially of the components as defined herein would not exclude trace contaminants from the isolation and purification method and pharmaceutically acceptable carriers. "Consisting of" shall mean excluding more than trace elements of other ingredients and substantial method steps for administering the compositions of this invention. Embodiments defined by each of these transition terms are within the scope of this invention.

As used herein, the term "optional" or "optionally" means that the subsequently described event or circumstance may or may not occur, and that the description includes instances where said event or circumstance occurs and instances where it does not.

As used herein, a "subject" refers to a mammal such as a primate, in one embodiment as a human. Non-human primates include marmosets, monkeys, chimpanzees, gorillas, orangutans, and gibbons, to name a few. The term "subject" includes cats, dogs, ferret, chinchilla, mouse, rabbit, rat, gerbil, guinea pig, cattle, horses, pigs, sheep, goats, chickens, turkeys, ducks, pheasants, pigeons, doves, parrots, cockatoos, geese, etc.

As used herein, a "subject in need" of the methods of the disclosure can be a subject suffering from a pain condition.

As used herein, the term "therapeutically effective" amount, refers to an amount of an active ingredient that is sufficient to induce a localized analgesic effect in a subject. The therapeutically effective amount of the pharmaceutical composition of the present disclosure may be effective in disrupting a lipid raft. The therapeutically effective amount of the pharmaceutical composition of the present disclosure may be effective in upregulating (e.g., stimulating) expression and/or secretion of leptin, M-CSF, G-CSF, GM-CSF etc. from a cell of the subject. The therapeutically effective amount of the pharmaceutical composition of the present disclosure may also be effective in downregulating (e.g., suppressing) expression and/or secretion of ATP, iNOS, PGE2, etc. from a cell of the subject. Alternatively stated, a "therapeutically effective" amount is an amount that will provide some alleviation, mitigation, decrease, or stabilization in at least one clinical symptom in the subject. Those skilled in the art will appreciate that the therapeutic effects need not be complete or curative, as long as some benefit is provided to the subject. The effective amount may vary depending on such factors as the wound or affected area, or the disease or condition being treated, the particular targeted constructs being administered, the size of the subject, or the severity of the disease or condition. One of ordinary skill in the art may empirically determine the effective amount of a particular composition without necessitating undue experimentation.

The term "active ingredient" used herein refers to a biologically active substance. In embodiments, the dicarboxylic acid ester of the present disclosure is the active ingredient in a pharmaceutical composition. In embodiments, the dicarboxylic acid ester of the present disclosure is the only active ingredient in a pharmaceutical composition. In embodiments, the azelaic acid ester of the present disclosure is the active ingredient in a pharmaceutical composition. In embodiments, diethyl azelate is the active ingredient in a pharmaceutical composition.

As used herein, the term "pharmaceutically acceptable carrier" refers to any suitable adjuvants, carriers, excipients, or stabilizers, and can be in solid or liquid form such as, tablets, capsules, powders, solutions, suspensions, or emulsions, that does not cause significant irritation to the subject and does not abrogate the biological activity and properties of the administered active ingredients.

As used herein, the term "disease" is intended to be generally synonymous, and is used interchangeably with the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, the "treating" or "treatment" of a disease or condition, may refer to preventing the disease or condition, slowing the onset or rate of development of the disease or condition, reducing the risk of developing the disease or condition, preventing or delaying the development of symptoms associated with the disease or condition, reducing or ending symptoms associated with the disease or condition, generating a complete or partial regression of the disease or condition, or some combination thereof. Treatment may also mean a prophylactic or preventative treatment of a disease or condition.

As used herein, the term "inhibiting" refers to a decrease, reduction, limiting, and/or blocking of a particular action, function, interaction, appearance of a symptom. The terms "inhibiting," "decreasing," and "reducing" are used interchangeably herein. In embodiments, the term refers to reducing or preventing the level of certain activities, functions, interactions, appearances of certain symptoms (e.g., levels of biomarkers including, but not limited to, proteinaceous or non-proteinaceous molecules in tissues and body fluids) in a subject to a quantity which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control. For example, pain is decreased, reduced, or inhibited, if an indicator of pain, e.g., blood levels of prostaglandin PGE2, is at least about 10%, 20%, 30%, 50%, 80%, or 100% reduced. In embodiments, the pain is decreased, reduced, or inhibited by at least about 1-fold, 2-fold, 3-fold, 4-fold, or more in comparison to the pain prior to administration of the dicarboxylic acid ester of the present disclosure. The measurable change may be objective (e.g., measurable by some test or marker, for example, in an in vitro or in vivo assay or test or observation, or subjective (e.g., the subject gives an indication of or feels an effect).

As used herein, the term "pain" refers to an unpleasant sensory and emotional experience associated with actual or potential tissue damage, or described in terms of such damage and includes the more or less localized sensation of discomfort, distress, or agony, resulting from the stimulation of specialized nerve endings. There are many types of pain, including, but not limited to, nociceptive pain, neuropathic pain, or nociplastic pain, whether acute or chronic. The goal of inducing an analgesic effect in a subject is to reduce the degree or severity of pain perceived by the subject.

As used herein, the phrase "localized pain" refers to non-systemic pain experienced at a particular location or area on a specific part of the body of a subject. In embodiments, the area of pain is related to a primary lesion.

In embodiments, the disclosure provides methods and pharmaceutical compositions for inducing an analgesic effect, thereby inhibiting pain in a subject, including administering to a subject a pharmaceutical composition including a dicarboxylic acid ester having the Formula I: $R_2OOC-(CH_2)_n-COOR_1$. In embodiments, n is between 4 and 10, between 6 and 9, or between 7 and 8. In embodiments, each $R_1$ and $R_2$ are independently a lower alkyl. The term "lower alkyl," as used herein, refers to a C1 to C6 saturated straight or branched alkyl group. Example of suitable lower alkyl groups ($R_1$ and $R_2$) in Formula I include methyl, ethyl, propyl, isopropyl, butyl, sec-butyl, t-butyl, and the like groups. In embodiments, $R_1$ and $R_2$ are the same. In embodiments, $R_1$ and $R_2$ are the same. In embodiments, $R_1$ and $R_2$ are different.

In embodiments, the dicarboxylic acid ester is an azelaic acid ester. In embodiments, the azelaic acid ester is diethyl azelate, dimethyl azelate, or mixtures thereof. In embodiments, the azelaic acid ester is diethyl azelate.

In embodiments, the disclosure provides a method for inducing an analgesic effect, thereby inhibiting pain in a subject, including administering to the subject a pharmaceutical composition including an azelaic acid ester. In embodiments, the disclosure provides a method for inducing an analgesic effect, thereby inhibiting pain in a subject, includes administering to the subject a pharmaceutical composition including diethyl azelate.

Inducing a localized analgesic effect may be accomplished by disrupting or increasing the fluidity of lipid rafts. Lipid rafts (also known as lipid microdomains) are discrete lipid domains present in the external leaflet of the plasma membrane. Lipid rafts are enriched in cholesterol, sphingomyelin, gangliosides, and sphingolipids such as monosialotetrahexosylganglioside1 (GM1). Lipid rafts influence membrane fluidity and membrane protein trafficking, thereby regulating neurotransmission and receptor trafficking. Z. Korade, et al., Neuropharmacology (2008) 55 (8): 1265-73.

In embodiments, the analgesic effect is induced due to the disruption of lipid rafts caused by contacting a dicarboxylic acid ester of Formula I with lipid rafts. When the dicarboxylic acid ester of Formula I is applied topically onto the subject (e.g., open wound, area around the wound, healthy skin, mucous membrane, oral mucosal wound), the dicarboxylic acid ester makes contacts with the lipid rafts located in the plasma membranes of the subject, disrupting the lipid rafts. In embodiments, the lipid raft contains GM1.

In embodiments, the lipid raft contains phospholipase D2 (PLD2).

In embodiments, the dicarboxylic acid ester of Formula I disrupts lipid raft containing GM1.

In embodiments, the disruption of the lipid raft by a dicarboxylic acid ester of Formula I caused PLD2 to depart the lipid raft, thereby activating TREK-1 and subsequently promoting the production of signaling lipid phosphatidic acid (PA).

In embodiments, the disruption of the lipid raft by a dicarboxylic acid ester of Formula I modulates the membrane fluidity of the lipid raft.

In embodiments, the disruption of the lipid raft by a dicarboxylic acid ester of Formula I is due to an increase of the plasma membrane fluidity of the lipid raft.

Pain can be subdivided by type in a variety of ways. On the basis of time, pain can be classed as chronic or acute. Chronic pain is recognized as pain that lasts past normal healing time, usually for more than 3 months. Chronic pain affects about 20% of people worldwide and accounts for about 20% of physician visits. [R. Treede, et al., Pain (2015) 156(6):1003-7]. On the basis of mechanism, pain can be nociceptive, neuropathic or nociplastic. Nociceptive pain results from stimulation of pain receptors for issue injury (nociceptors) due to mechanical, chemical, or thermal stimuli. Neuropathic pain results from damage to components of the nervous system. Nociplastic pain arises from an alteration of nociceptive perception.

In embodiments, the subject is suffering from a pain. In embodiments, the pain is acute or chronic. In embodiments, the pain is nociceptive pain, neuropathic pain, or nociplastic pain.

In embodiments, the pain is acute. In embodiments, the subject can be in need of treatment for acute pain. Examples of acute pain include, but are not limited to, traumatic pain, procedural (surgery, dental, dermatologic, etc.) pain, wound pain, musculoskeletal pain (e.g., back pain, neck pain), toothache, infection (e.g., wound infection), and toxins (insect, animal, bacterial, fungal, etc.).

In embodiments, the pain is chronic. In some embodiments, the subject can be in need of treatment for chronic pain. Examples of chronic pain include, but are not limited to, fibromyalgia, arthritis pain, iliotibial band syndrome pain, tennis elbow pain, cancer pain, musculoskeletal pain (e.g., back pain, neck pain), temporomandibular joint disorder, trigeminal neuralgia, chronic headaches, pain associated with neurologic diseases (MS, diabetic neuropathy, etc.), neuroma, pelvic inflammatory disease, endometriosis, shingles and post-herpetic neuralgia, and infection (e.g., HIV) associated chronic neuropathy, chemotherapy-induced neuropathic pain, surgery-induced neuropathic pain, trauma-induced neuropathic pain, vulvodynia, atypical craniofacial pain, sciatica, phantom limb, odontalgia, and burning mouth syndrome.

In embodiments, the pain is nociceptive pain. In embodiments, the subject can be in need of treatment for nociceptive pain. Nociceptive pain is usually acute and develops in response to a specific situation. Examples of nociceptive pain include, but are not limited to, pain from sprains, burns, bruises, surgical procedures and bone fractures. Chronic nociceptive pain results from some conditions when pain extends beyond six months. Examples of chronic nociceptive pain include pain from cancer, rheumatoid arthritis, osteoarthritis, musculoskeletal conditions (e.g., back pain).

In embodiments, the pain is neuropathic pain. In embodiments, the subject can be in need of treatment for neuropathic pain. Neuropathic pain results from damage to components of the nervous system. Certain disease conditions can be the underlying cause of neuropathic pain. For example, a subject may be suffering from a metabolic disease (e.g., diabetic neuropathy), an autoimmune disease (e.g., multiple sclerosis), a viral infection (e.g., shingles and sequelae, postherpetic neuralgia), vascular disease (e.g., stroke), trauma and/or cancer. Campbell et al., Neuron (2006) 52(1):77-92; Dworkin et al., Arch Neurol (2003) 60; 1524-34. In embodiments, the neuropathic pain is due to nerve damage arising from metabolic disease, trauma, ischemia or hemorrhage, inflammation, neurotoxicity, neurodegeneration, paraneoplastic, vitamin deficiency, or cancer. Examples of neuropathic pain include, but are not limited to, post herpetic (or post-shingles) neuralgia, reflex sympathetic dystrophy/causalgia (nerve trauma), components of cancer pain, phantom limb pain, entrapment neuropathy (e.g., carpal tunnel syndrome), and peripheral neuropathy (widespread nerve damage).

In embodiments, the pain is nociplastic pain. In embodiments, the subject can be in need of treatment for nociplastic pain. Nociplastic pain is pain that arises from altered nociception despite no clear evidence of actual or threatened tissue damage causing the activation of peripheral nociceptors or evidence for disease or lesion of the somatosensory system causing the pain. Chimenti et al., Phys Ther. (2018) 98(5): 302-314.

In embodiments, the pain is selected from acute pain, chronic pain, nociceptive pain, neuropathic pain, nociplastic pain, traumatic pain, chemical pain, burn pain, ischemic pain, insect bite pain, prickling pain, musculoskeletal pain (e.g., back pain, neck pain), rheumatoid arthritis pain, post-surgical pain, bone pain (e.g., osteoarthritis), pain due to various skin conditions (e.g., acne, psoriasis, hidradenitis suppurativa, eczema, rosacea).

In embodiments, the dicarboxylic acid ester of Formula I is administered in an amount sufficient to induce an analgesic effect in a subject, such that to reduce a pain response. In embodiments, the dicarboxylic acid ester of Formula I is administered in an amount sufficient to reduce a pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In embodiments, the dicarboxylic acid ester of Formula I is administered in an amount sufficient to induce an analgesic effect in a subject, such that to reduce a pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In embodiments, the dicarboxylic acid ester of Formula I is administered in an amount sufficient to induce an analgesic effect in a subject, such that to reduce a pain response mediated by a nociceptive pain, a neuropathic pain, or a nociplastic pain. In embodiments, the dicarboxylic acid ester of Formula I is administered in an amount sufficient to reduce a pain response a nociceptive pain, a neuropathic pain, or a nociplastic pain by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In embodiments, the dicarboxylic acid ester of Formula I is administered in an amount sufficient to induce an analgesic effect in a subject, such that to reduce a pain response mediated by a nociceptive pain, a neuropathic pain, or a nociplastic pain in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In embodiments, the present disclosure provides methods of modulating one or more pattern recognition receptor signaling, such as pattern recognition receptors including nucleotide oligomerization domain (NOD) receptors, and Dectin receptors in a subject in need, comprising administering to the subject a therapeutically effective amount of the dicarboxylic acid ester of Formula I. In embodiments, the reduction of pain (or the reduction of a pain response) is due to the modulation of PRR associated pain activity.

In embodiments, the reduction of pain (or the reduction of a pain response) is due to the modulation of PRR activity.

In embodiments, the reduction of a pain response (or the reduction of a pain response) is due to the modulation of NOD receptor activity.

In embodiments, the reduction of a pain response (or the reduction of a pain response) is due to the modulation of Dectin receptor activity.

In embodiments, the present disclosure provides methods of inducing an analgesic effect, thereby modulating pain in a subject in need, by administering to the subject a pharmaceutical composition including a therapeutically effective amount of dicarboxylic acid ester of Formula I to promote the synthesis or release or upregulate one or more of leptin, macrophage colony-stimulating factor (M-CSF), granulocyte colony-stimulating factor (G-CSF), granulocyte macrophage colony-stimulating factor (GM-CSF).

In embodiments, the present disclosure provides methods of inducing an analgesic effect, thereby modulating pain in a subject in need, by administering to the subject a pharmaceutical composition including a therapeutically effective amount of a dicarboxylic acid ester of Formula I to inhibit the synthesis or release, or downregulate the activity and/or expression of at least one of at least one of inducible nitric oxide synthase (iNOS), adenosine triphosphate (ATP) and prostaglandin E2 (PGE2).

In embodiments, the disclosure provides methods of inducing an analgesic effect, thereby treating a subject suffering from pain, including administering to the subject a pharmaceutical composition including a dicarboxylic acid ester of Formula I, by promoting a localized increase at the site of administration of one or more of leptin, M-CSF, G-CSF, GM-CSF, or decrease of iNOS, ATP and PGE2 in a subject.

In embodiments, the dicarboxylic acid ester of Formula I is administered to a subject in need an amount sufficient to induce release or upregulate the activity and/or expression of one or more of leptin, M-CSF, G-CSF, and GM-CSF.

In embodiments, the dicarboxylic acid ester of Formula I is administered to a subject in need an amount sufficient to suppress release or downregulate the activity and/or expression of at least one of iNOS, ATP and PGE2.

Synthesis of Dicarboxylic Acid Esters

The dicarboxylic acid ester of Formula I may be obtained commercially or prepared by various methods known in the art. In embodiments, the dicarboxylic acid ester can be prepared via direct formation of the ester from the requisite acid and an alcohol. This condensation may be achieved by the dehydration of the reaction mixture with a suitable agent or by heating a mixture of the acid and alcohol. In embodiments, the dicarboxylic acid ester can be prepared by reacting an alcohol with an activated form of the acid. Activated forms of the acid include acid halides, acid anhydrides including both homo and hetero anhydrides, the reaction of the internal anhydride of the parent acid with the requisite alcohol, esters and anhydrides of both the acid and the alcohol which are formed by reaction of the requisite acid or alcohol with p-toluene sulfonyl chloride to produce the tosyl anhydride or ester which is subsequently reacted with the alcohol or acid respectively to produce the desired final ester. Similarly, one could substitute a simple organic acid anhydride, such as acetic acid anhydride, for the p-toluene sulfonyl chloride. In addition, one could start with one ester selected from among the desired compositions of matter and by the means of solution of the ester in a desired alcohol in the presence of an appropriate acidic or basic catalyst effect a conversion of the starting ester of the acid to an ester wherein the alcohol becomes that in which the reaction is carried out which method is also known to the art as trans-esterification.

For example, one could start with the dimethyl ester of the acid and by solution of the ester in ethanol in the presence of an acid or base one could cause the facile formation of the diethyl ester of the acid. In addition, if a mixed ester of the acid were desired, one could utilize an appropriately composed solution of the two or more desired alcohols in any of the methods herein described.

One could resort to the use of halogenated intermediates or ingredients to form the required esters. For example, thionyl chloride will chlorinate both acids and alcohols, thereby resulting in the acyl and alkyl chlorides. These acyl and alkyl chlorides may then be further reacted with the desired alcohol or acid respectively to produce the desired ester products. Other common halogenating agents include for example oxalyl chloride and the chlorides and bromides of phosphorous such as phosphorous penta or trichloride and penta or tribromide or phosphorous oxychloride.

It is commonly practiced to form esters through the action of a strong base on a mixture of the acid and the alcohol. Examples of strong bases include lithium aluminum hydride and other metal hydrides, alkali metal alkoxides such as sodium ethoxide and diisobutyl aluminum hydride and so on.

Methods of Administration

The pharmaceutical composition of the present disclosure may be administered to a subject in a variety of ways. For example, the pharmaceutical compositions can be administered topically, transdermally, intravenously, subcutaneously, intramuscularly or orally. The pharmaceutical composition may be applied locally at and/or around the target area or the area where treatment is desired.

The treatment regime can vary depending upon various factors typically considered by one of ordinary skill in the art. These factors include the route of administration, the nature of the formulation, the nature of the patient's illness, the subject's size, weight, surface area, age, gender, other drugs being administered to the patient, and the judgment of the attending physician. The pharmaceutical compositions can be administered along with or in addition to other treatments for an inflammatory condition or pain reduction.

The pharmaceutical compositions can be administered in combination with one or more additional therapeutic agents for the treatment of pain and/or inflammation. The one or more additional therapeutic agents may be administered by the same or different routes of administration. The one or more additional therapeutic agents may include pain relievers, anti-inflammatory agents, anesthetic agents, antibiotics, and antifungals.

In embodiment, the pharmaceutical composition is administered to a subject topically on the skin of the subject, for example, in areas located at or at least within the vicinity of an area where treatment is desired. In embodiment, the pharmaceutical composition is administered to a subject by rubbing it topically against the skin, which allows the composition (or at least, the dicarboxylic acid ester) to be absorbed by the skin.

In embodiments, for prophylactic treatments, the pharmaceutical compositions can be administered to a subject at a time period of from 96 hours to immediately before, from 72 hours to immediately before, from 48 hours to immediately before, from 24 hours to immediately before, from 12 hours to immediately before, from 8 hours to immediately before, from 4 hours to immediately before, from 2 hours to immediately before, from 1 hour to immediately before, or from 0.5 hour to immediately before a procedure (or surgery), or any range derivable therein immediately before the procedure. The pharmaceutical compositions may be applied topically to an area of healthy skin, at any time, for example, in one embodiment, before hiking.

In embodiment, for purpose of prophylactic treatments, the pharmaceutical composition is administered to a subject locally or topically prior to a procedure, such as, a venipuncture, an injection, incision, hair removal, tattoo application and removal.

In embodiment, the pharmaceutical composition is administered to a subject locally or topically during or after a procedure, such as, a venipuncture, an injection, incision, hair removal, tattoo application and removal.

In embodiment, the pharmaceutical composition is applied once, or more than once to a subject. For example, the pharmaceutical composition may be administered at predetermined intervals. In embodiments, for instance, the pharmaceutical composition may be applied once per day, twice per day, 3 times per day, 4 times per day, or more than 4 times per day, or once every other day, once every three days, once every four days, etc.

In embodiment, the pharmaceutical composition is administered to the subject in a therapeutically effective dose. When administered to a subject, therapeutically effective amounts will depend on the particular condition being treated and the desired outcome.

The pharmaceutical compositions can be administered to a subject in need at about every 1 to about 24 hours, about every 1 to about 12 hours, about every 2 to about 8 hours, about every 2 to about 6 hours, about every 4 to about 6 hours, about every 4 to about 8 hours, about every 12 hours, about every 24 hours, about every 48 hours, or more often. In embodiments, the pharmaceutical composition can be administered once, twice, three times, four times, five times, six times, seven times, eight times, or more often daily, or any combination thereof. In embodiments, the pharmaceutical composition can also be administered daily, every other day, every two days, every three days, every four days, or less often, or any combination thereof. In embodiments, the pharmaceutical composition can be administered to a subject in need for a duration of from 1 day to 30 days, from 1 day to 25 days, from 1 day to 20 days, from 1 day to 15 days, or from 1 day to 10 days.

Formulations

In embodiments, the pharmaceutical compositions of the disclosure can be formulated for delivery via any route of administration known in the art, including but not limited to topical, transdermal, intravenous, subcutaneous, intramuscular, or oral administration.

Proper formulation is dependent upon the route of administration chosen. Any of the well-known techniques, carriers, and excipients as understood in the art may be used e.g., those disclosed in Remington's Pharmaceutical Sciences, 18th ed, (Mack Publishing Company: Easton, Pa., 1990) incorporated herein by reference. The pharmaceutical compositions disclosed herein may be manufactured in any manner known in the art, such as by means of conventional mixing, dissolving, granulating, levigating, emulsifying, encapsulating, entrapping or compression processes.

The pharmaceutical compositions include those suitable for topical, transdermal, intravenous, subcutaneous, intramuscular, or oral administration, although the most suitable route may depend upon, for example, the condition and disorder of the recipient.

In embodiments, the pharmaceutical composition is suitable for topical and transdermal administrations. Topical and transdermal administration of azelaic acid esters of the present disclosure can be in the form of a processed gel, cream, lotion, solution, ointment, suspension, or emulsion. These pharmaceutical compositions may further include one or more suitable excipient disclosed herein.

Parenteral administration, such as intravenous, subcutaneous, intramuscular administration of a dicarboxylic acid ester of Formula I can be in the form of solutions, suspensions, or emulsions. In one embodiment, these formulations are prepared in a saline solution. These pharmaceutical compositions may further include one or more suitable excipient disclosed herein.

In embodiments, the pharmaceutical composition is suitable for oral administration. The pharmaceutical compositions may conveniently be presented in unit dosage forms and may be prepared by any of the methods well known in the art of pharmacy. Typically, these methods include the step of mixing a dicarboxylic acid ester of Formula I, and optionally any co-administered active ingredient, with the carrier which constitutes one or more accessory ingredients. In general, the pharmaceutical compositions are prepared by uniformly and intimately mixing the active ingredients with liquid carriers or finely divided solid carriers or both and then, as necessary, shaping the product into the desired composition. The pharmaceutical composition and any optional secondary active ingredient, suitable for oral administration may be presented as discrete units such as capsules, cachets or tablets each containing a predetermined amount of the active ingredient(s); as a powder or granules; as a solution or a suspension in an aqueous liquid or a non-aqueous liquid; or as an oil-in-water liquid emulsion or a water-in-oil liquid emulsion. The active ingredient(s) may also be presented as a bolus, electuary or paste. These pharmaceutical compositions may further include one or more suitable excipient disclosed herein.

Excipients

In embodiments, the pharmaceutical composition of the disclosure may further include one or more excipients. The excipient may include a carrier, for example, water-insoluble polysaccharide or oligosaccharide. Examples of carriers include, but are not limited to, cellulose acetate, cellulose acetate butyrate, cellulose acetate propionate, cellulose acetate phthalate, chitosan, β-cyclodextrin, ethyl cellulose, hydroxypropylmethyl cellulose phthalate (HPMCP), microcrystalline cellulose, starch, and any combination thereof.

The excipient may include a thickening agent, for example, a water-soluble polysaccharide. Examples of thickening agents include, but are not limited to, hydroxy propyl methyl cellulose (HPMC), acacia, alginic acid, colloidal silicone dioxide, carboxymethylcellulose calcium, gelatin, hydroxy propyl cellulose, hydroxyl propyl cellulose (hypromellose), methyl cellulose, sucrose, sodium alginate, sodium carboxy methyl cellulose, and any combination thereof.

In embodiments, the pharmaceutical composition of the disclosure may further include one or more pharmaceutical excipients, for example ascorbic acid, EDTA dihydrate, glycerin, citric acid monohydrate, sodium citrate dihydrate, sodium benzoate, sodium propionate, 70% sorbitol solution, sucralose, FD&C Yellow #6, artificial flavor (e.g., artificial peppermint flavor, artificial fruit flavor), purified water, or any combination thereof.

In embodiments, the pharmaceutical composition of the disclosure may include a preservative, Suitable preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; benzoic acid, benzyl alcohol and sorbic acid and salts thereof.

In embodiments, the pharmaceutical composition of the disclosure may include one or more acceptable pH adjusting agents and/or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in a pharmaceutically acceptable range. In embodiments, the pH of the pharmaceutical composition of the disclosure may be from pH 4 to pH 7.5.

In embodiments, the pharmaceutical composition of the disclosure may include a sugar alcohol. Examples of sugar alcohols include, but are not limited to, mannitol, glycerol, galactitol, fucitol, inositol, volemitol, maltotriitol, maltoetetraitol, polyglycitol, erythritol, threitol, ribitol, arabitol, xylitol, allitol, dulcitol, glucitol, sorbitol, altritol, iditol, maltitol, lactitol, isomalt, and any combination thereof.

In embodiments, the pharmaceutical composition of the disclosure may include an additive. Examples of additives include, but not limited to, diluents, binders, surfactants, lubricants, glidants, coating materials, plasticizers, coloring agents, flavoring agents, or pharmaceutically inert materials. Examples of diluents include, for example, cellulose; cellulose derivatives such as microcrystalline cellulose and the like; starch; starch derivatives such as corn starch, cyclodextrin and the like; sugar; sugar alcohol such as lactose, D-mannitol and the like; inorganic diluents such as dried aluminum hydroxide gel, precipitated calcium carbonate, magnesium aluminometasilicate, dibasic calcium phosphate and the like. Examples of binders include, for example, hydroxypropylcellulose, methylcellulose, hydroxypropylmethylcellulose (hydroxypropyl methylcellulose), povidone, dextrin, pullulane, hydroxypropyl starch, polyvinyl alcohol, scacia, agar, gelatin, tragacanth, macrogol and the like. Examples of surfactants include, for example, sucrose esters of fatty acids, polyoxyl stearate, polyoxyethylene hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, lauromacrogol, quaternary ammonium salts (e.g., Benzyldimethyltetradecylammonium Chloride Hydrate, Benzethonium Chloride, Benzylcetyldimethylammonium Chloride Hydrate, Benzyldimethylstearylammonium Chloride Hydrate, Benzyldodecyldimethylammonium Chloride Dihydrate, Benzyldodecyldimethylammonium Bromide), and the like. Examples of lubricants include, for example, stearic acid, calcium stearate, magnesium stearate, talc and the like. Examples of glidants include, for example, dried aluminum hydroxide gel, magnesium silicate and the like. Examples of coating materials include, for example, hydroxypropylmethyl cellulose 2910, aminoalkyl methacrylate copolymer E, polyvinylacetal diethylaminoacetate, macrogol 6000, titanium oxide and the like. Examples of plasticizers include, for example, triethyl citrate, triacetin, macrogol 6000 and the like.

In embodiments, the pharmaceutical composition of the disclosure includes a therapeutically effective amount of dicarboxylic acid ester of Formula I and a pharmaceutical acceptable carrier. In embodiments, the pharmaceutical composition includes a therapeutically effective amount of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% dicarboxylic acid ester of Formula I based on the total weight of the formulation. In embodiments, the pharmaceutical composition includes a therapeutically effective amount of from about 5% to about 100% by weight, from about 5% to about 95% by weight, from about 5% to about 90% by weight, from about 5% to about 85% by weight, from about 5% to about 80% by weight, from about 5% to about 75% by weight, from about 5% to about 70% by weight, from about 10% to about 100% by weight, from about 10% to about 95% by weight, from about 10% to about 90% by weight, from about 10% to about 85% by weight, from about 10% to about 80% by weight, from about 10% to about 75% by weight, from about 10% to about 70% by weight, from about 15% to about 100% by weight, from about 15% to about 95% by weight, from about 15% to about 90% by weight, from about 15% to about 85% by weight, from about 15% to about 80% by weight, from about 15% to about 75% by weight, from about 15% to about 70% by weight, from about 20% to about 100% by weight, from about 20% to about 95% by weight, from about 20% to about 90% by weight, from about 20% to about 85% by weight, from about 20% to about 80% by weight, from about 20% to about 75% by weight, from about 20% to about 70% by weight, from about 25% to about 100% by weight, from about 25% to about 95% by weight, from about 25% to about 90% by weight, from about 25% to about 85% by weight, from about 25% to about 80% by weight, from about 25% to about 75% by weight, from about 25% to about 70% by weight, from about 30% to about 100% by weight, from about 30% to about 95% by weight, from about 30% to about 90% by weight, from about 30% to about 85% by weight, from about 30% to about 80% by weight, from about 30% to about 75% by weight, from about 30% to about 70% by weight, from about 35% to about 100% by weight, from about 35% to about 95% by weight, from about 35% to about 90% by weight, from about 35% to about 85% by weight, from about 35% to about 80% by weight, from about 35% to about 75% by weight, from about 35% to about 70% by weight, from about 40% to about 100% by weight, from about 40% to about 95% by weight, from about 40% to about 90% by weight, from about 40% to about 85% by weight, from about 40% to about 80% by weight, from about 40% to about 75% by weight, from about 40% to about 70% by weight, from about 45% to about 100% by weight, from about 45% to about 95% by weight, from about 45% to about 90% by weight, from about 45% to about 85% by weight, from about 45% to about 80% by weight, from about 45% to about 75% by weight, from about 45% to about 70% by weight, from about 50% to about 100% by weight, from about 50% to about 95% by weight, from about 50% to about 90% by weight, from about 50% to about 85% by weight, from about 50% to about 80% by weight, from about 50% to about 75% by weight, from about 50% to about 70% by weight, from about 55% to about 100% by weight, from about 55% to about 95% by weight, from about 55% to about 90% by weight, from about 55% to about 85% by weight, from about 55% to about 80% by weight, from about 55% to about 75% by weight, from about 55% to about 70% by weight, from about 60% to about 100% by weight, from about 60% to about 95% by weight, from about 60% to about 90% by weight, from about 60% to about 85% by weight, from about 60% to about 80% by weight, from about 60% to about 75% by weight, from about 60% to about 70% by weight of dicarboxylic acid ester of Formula I based on the total weight of the formulation.

In embodiments, the pharmaceutical composition of the disclosure includes a dicarboxylic acid ester of Formula I may be formulated and incorporated into all pharmaceutical dosage forms known to those skilled in the art. Such pharmaceutical compositions may be used in cells, tissues and organs of a subject in need of the treatment and to be administered over a wide range of doses. In embodiments, dicarboxylic acid esters of the disclosure may be administered to the subject orally, parenterally, topically and locally, in a daily dosage of 0.001 mg/kg to 1000 mg/kg body weight per day.

Kits

In embodiments, the disclosure also provides a kit that includes a pharmaceutical composition of the present disclosure, especially for topical administration, a wipe to clean the site, a swab or brush to spread the applied material, an adhesive dressing to cover the site; optionally, the kit may include a disposal bag or container; optionally, the kit may include an absorbent element; optionally, the kit may include a pair of gloves (e.g., sterile nitrile or latex gloves).

EXAMPLES

Materials and Methods

Chemicals: Diethyl azelate (>99% purity) was synthesized from azelaic acid and ethyl alcohol using acid-catalyzed esterification followed by fractional distillation to 99% purity as determined by gas chromatography-mass spectrometry (GC-MS). Unless stated otherwise, the chemicals were sourced from Sigma Chemical (St. Louis, MO, USA) and Thermo Fisher Scientific (Waltham, MA).

Cell proliferation and cytotoxicity assays: CellTiter 96 Non-Radioactive Cell Proliferation Assay (MTT), CellTiter 96 AQueous One Solution Cell Proliferation Assay (MTS) and CellTiter-Glo Luminescent Cell Viability (ATP) kits were purchased from Promega (Madison, WI). Protein concentration was measured using Micro BCA protein assay kit (Pierce Biotechnology, Rockford, IL).

Isolation of human peripheral blood mononuclear cells: Fresh human peripheral blood mononuclear cells (PBMC) specimens were obtained from healthy volunteers. The blood was collected into BD Vacutainer CPT Cell Preparation Tubes (Beckton Dickinson, Franklin Lakes, NJ) and centrifuged at 1,500×g at room temperature and PBMCs were isolated according to supplier's protocol. Cell counts and viability assessment using trypan blue exclusion were measured using hemocytometer.

Membrane fluidity measurements: Membrane fluidity was measured using Membrane Fluidity Kit (PN M0271, Marker Gene Technologies, Eugene, OR). PBMCs were washed and adjusted to 7×105 cells/mL in phenol-red free RPMI cell culture medium with 10% fetal bovine serum (FBS). Sixty thousand PBMCs per well were plated in triplicate in 96-well Acrowell filter plates (Pall Corporation, Port Washington, NY) and treated with 1 µM pyrenedecanoic acid alone or in the presence of the test articles (DEA from 100 µM to 0.1 µM or 10 µM cholesterol) with gentle mixing in the dark for 20 min. The fluorescence of the excimer (excitation at 355 nm, emission at 460 nm) was corrected for the monomer (excitation at 355 nm, emission at 400 nm).

Multiplexed immunoassays: Human and murine cytokine, chemokine and growth factors panels (including leptin and colony-stimulating factors G-CSF, GM-CSF, and M-CSF) were obtained from Affymetrix, Fremont, CA Specimens were assayed in duplicate or triplicate as described for murine assay [R. Streeper, et al., Current Topics in Nutraceutical Research (2011) 9:1-12] and human assay [E. Izbicka, et al., Cancer Genomics Proteomics (2012) 9(1): 27-35]. Multiplexed immunoassays were performed using Luminex 100 IS System (Luminex Corporation, Austin, TX). Analyte concentrations were calculated from the standard curves using Bio-Plex Manager 4.1.1 (Bio-Rad Laboratories, Hercules, CA).

Pathogen-associated molecular pattern receptor agonist studies: PRR agonist kits; human Toll-like receptor (TLR1-9; n=9 agonists), nucleotide oligomerization domain (NOD) NOD1/NOD2 (n=10 agonists, denoted n1, n2, . . . , n10) and dectin-1 (a single agonist) were purchased from InvivoGen, San Diego, CA Plasmacytoid human dendritic cells (MatTek Corporation, Ashland, MA) were diluted to $1.6 \times 10^5$ cells/mL and incubated with the agonists at the concentrations in the middle ranges recommended by the supplier in the absence of DEA or with 0.5% DEA for 24 hours. The levels of measured analytes were normalized to the numbers of viable cells.

chemokines, and growth factors, DEA downregulated most of the pro-inflammatory markers. Croton oil (a chemical irritant) was used as a control. The results are shown as percent difference in marker levels in tissues treated with the test articles and those treated with croton oil alone. (Table 1). As shown in Table 1, DEA simultaneously upregulated anti-inflammatory cytokines IL-4, IL-10, IL-13 and IL-1ra. Moreover, DEA also inhibited PGE2 and increased levels of leptin, GM-CSF and G-CSF. This pattern of tandem upregulation of examined markers in concert with downregulation of PGE2 was unique for DEA and was not observed with any other test article.

TABLE 1

DEA simultaneously upregulates anti-inflammatory markers, leptin and colony stimulating factors and downregulates PGE2 in EpiDerm tissues exposed to croton oil insult (control). The results are expressed as percentages of the control.

| Test article | IL-4 | IL-10 | IL-13 | IL-1ra | PGE2 | Leptin | GM-CSF | G-CSF |
|---|---|---|---|---|---|---|---|---|
| DEA | 600 | 200 | 112 | 33 | −281 | 51 | 280 | 561 |
| Azelaic acid | 40 | 152 | −4 | 18 | −1 | 41 | −16 | −100 |
| Salicylic acid | 40 | 257 | −46 | 15 | 5 | 202 | −7 | 640 |
| Green tea extract | 80 | 71 | −31 | 6 | −8 | 27 | −7 | 140 |
| Doxorubicin | 80 | 214 | −38 | 15 | −2 | 116 | −3 | 0 |
| 4-ethoxybenzaldehyde | 80 | 471 | 34 | 34 | 4 | 39 | −26 | 340 |
| Retinoic acid | 100 | 369 | −19 | 20 | 4 | 36 | −39 | 360 |

RESULTS

Example 1

This experiment demonstrates that DEA modulates biomarkers of pain signaling in human EpiDerm tissues.

EpiDerm Bioassays: The EpiDerm™ 3-Dimensional Skin Model was purchased from MatTek Corporation (Ashland, MA). Test articles: 25% DEA, 25% azelaic acid sodium salt, 1% salicylic acid sodium salt, 1% green tea extract, 1 μg/mL doxycycline hyclate (doxorubicin), 1%, 4-ethoxybenzaldehyde, and 0.025% all-trans retinoic acid, were tested in triplicate up either alone or in combination with 0.1% croton oil used as an irritant for 24 hours. Conditioned media were collected, the remaining cells were homogenized on ice in the presence of protease and phosphatase inhibitors, and the lysates were clarified by centrifugation. The media and cell lysates were snap frozen at −70° C. Proteins were resolved by gel electrophoresis and visualized in immunoblots with human-specific antibodies to inducible nitric oxide synthase (iNOS), S-nitrosocysteine, and superoxide dismutase 2 (all from Abcam, Cambridge, MA).

EpiDerm is a 3-dimensional human tissue construct of non-transformed human keratinocytes that exhibit in vivo-like morphological and growth characteristics that allow topical application to the surface of the tissue which mimics the route of human exposure.

When the EpiDerm tissues were exposed to 0.1% croton oil used as a chemical irritant, the treatment with 25% DEA nullified croton oil irritant toxicity in proliferation and viability assays, and protected tissue integrity as evaluated by a microscopic inspection. Cellular signaling experiments compared the effects of DEA and other compounds commonly used in topical formulations: azelaic acid, salicylic acid, green tea extract, doxorubicin, 4-ethoxybenzaldehyde and all-trans retinoic acid. Among 57 examined cytokines, Example 2

This experiment demonstrates that DEA modulates cellular signaling from pattern recognition receptors.

The inventors of the present disclosure have shown that altered membrane protein function with a U-shaped dose response. At the concentration of 0.5% DEA increased membrane fluidity by 18% above the cholesterol control level. Physiological consequences of DEA membrane fluidizing activity were further investigated in human plasmacytoid dendritic cells, which express multiple PRRs including TLRs, NOD and dectin-1 receptors. Human plasmacytoid dendritic cells were stimulated with the receptor agonists alone or in combination with 0.5% DEA.

Human plasmacytoid dendritic cells ($1.6 \times 10^5$/ml) were exposed to 20 different PRR agonists alone at the concentrations within physiological ranges of each agonist or in the presence of 0.5% DEA for 24 hours. The results are expressed as the ratios of secreted ATP from the cells treated with the PRR receptor agonists and DEA (treatment groups) to the levels of ATP secreted by the cells treated with the agonists alone (control groups). The agonists are arranged according to their respective receptor localization on the cell surface or inside the cells. Extracellular levels were measured, and the results were expressed as the ratios of released ATP from the cells+receptor agonist+DEA to the ATP from the cells+receptor agonist alone. As shown in FIG. 1, the ATP ratios were <1 in all cases except for two NOD receptor ligands (n9 and n10) where DEA had no apparent effect on ATP signaling, but effectively competed with the two NOD ligands based on differential cytokine patterns in the presence and absence of DEA.

Referring to FIG. 1, DEA competed with all examined PRR agonists. The effect of DEA was greater on the cell surface receptors than on those located in the interior of the cells, and also greater for multimeric receptors (TLRs and dectin-1) compared to the monomeric NOD receptors. It has been further demonstrated that DEA downregulated cellular signaling from all examined PRR with unique and distinct patterns for each examined receptor agonist.

As disclosed herein, the finding of the ability of DEA to compete with all examined PRR agonists with profound effects on cellular signaling is unexpected and unprecedented.

Example 3

This experiment demonstrates that topical DEA increased latency of the response to a nociceptive heat stimulus in vivo.

In vivo studies: Animal studies and all procedures were performed in compliance with the Animal Welfare Act Regulations (9 CFR 3) and the NIH guidelines for the care and use of laboratory animals at New Frontier Labs LLC, San Antonio, TX Both male and female Balb/c mice 8-10 weeks old weighing approximately 25 g were purchased from Taconic Farms (Hudson, NY). Animals were acclimatized for at least 72 hours after delivery. Prior to experiments the animals were randomized into treatment and control groups. For the assessment of nociceptive effect of DEA, only male mice were used (n=8 per group). The hot plate test was performed at a constant temperature of 42° C. as described in S. Hunskaar, et al., Eur. J. Pharmacol. 1985; 111(2):221-6, which is incorporated herein by reference. DEA was administered neat (100%) or diluted in ethanol (vehicle) to the hind limb. The treatments were administered 5 minutes prior to the heat test. The time between the heat exposure to the first incidence of animal licking the hind paw was measured with a stopwatch.

Statistical analysis: Statistical analysis was done using Student t statistic; p values <0.05 were considered significant. All samples/data were included in the analysis. Continuously distributed outcomes were summarized with the mean and standard deviation. All statistical testing was two-sided with a nominal and experiment-wise significance level of 5% using SAS Version 9.2.

A nociceptic heat stimulus can induce pain and the threshold of 40° C. and above is used in testing effects of therapeutic analgesics in rodents as described in S. Hunskaar, et al., Eur J Pharmacol. (1985) 111(2):221-6. FIG. 2 summarizes the results of the effect of DEA on heat sensitivity in mice. There was an apparent dose response in the protective effect of DEA as demonstrated by the increased latency of the response. At the highest concentration of 100% DEA decreased heat sensitivity by 33% and the difference between this concentration of DEA and the untreated control was statistically significant (p=0.03). The extent of the pain protection elicited by topical DEA is comparable to acetylsalicylic acid and paracetamol applied intraperitoneally Hunskaar, et al., Behav. Brain Res. (1986) 21(2):101-8.

Transdermal adsorption of topical analgesics often limits their efficacy E. Beetge, et al., Int J Pharm. (2000) 193(2): 261-4. Physicochemical properties of DEA combined with an exceptional safety and efficacy profile favor its use in topical pain management.

Example 4

This experiment demonstrates that DEA abolishes assembly of cholera toxin subunits on PBMC plasma membranes.

Lipid rafts visualization: Fluorescent labeling of lipid rafts in human PBMCs was done using Vybrant Alexa Fluor 488 Lipid Rafts Labeling Kit (PN V-34403, Life Technologies, Grand Island, NY). PBMCs ($1\times10^6$ cells in 0.2 mL RPMI medium with 10% FBS in the absence or the presence of 0.5% DEA, quadruplicate repeats) were labeled with the fluorescent cholera toxin subunit B (CT-B) conjugate in for 10 minutes at 4° C., transferred to poly-lysine coated coverslips, washed with cold phosphate buffered saline, and cross-linked with the anti-CT-B antibody according to the supplier's instructions. The cells were fixed in 4% formaldehyde, washed with cold phosphate buffered saline with 0.1% bovine serum albumin and mounted in dry Vectashield. Images were acquired by confocal microscopy, fluorescent imaging was done using argon laser illumination, and analyzed using ImageJ software version 1.53e (ImageJ.nih.gov).

The modulation of lipid raft-associated proteins by DEA was investigated using cholera toxin, a multimeric $AB_5$ toxin produced by *Vibrio cholerae*. The B subunit of the toxin binds to cell surface GM1 ganglioside receptors. The receptor bound B subunits are localized to membrane microdomains referred to as lipid rafts, where they form pentameric membrane attack complexes. The A subunit of the toxin binds to the pentamer of membrane receptor bound B subunits and the complex is internalized via endocytosis releasing the toxic A subunit into the cytoplasm. The integrity of the lipid rafts is necessary for the cholera toxin to exert its toxic activity (S. Ray, et al., J. Biol. Chem. 2012; 287(36):30395-405).

To examine the effect of DEA on the formation of the membrane attack complex, human PBMCs were exposed to fluorescently labeled cholera toxin B subunit (1) with treatment with DEA, and (2) without treatment with DEA. Phase contrast microscopy was used to visualize individual cells while the fluorescence microscopy allowed visualization of the cell-bound cholera toxin B subunit. FIG. 3 shows representative images of control cells without DEA treatment (left column) and with DEA treatment (right column). Phase contrast and the corresponding fluorescence images are shown in the upper and lower rows, respectively. Most of the control cells (77%) displayed fluorescent rings on their perimeters with foci of enhanced fluorescence. In contrast, DEA-treated PBMCs showed faint diffuse fluorescence spread evenly over the surfaces of the plasma membranes and no foci of enhanced fluorescence were detectable.

These results suggest that DEA disrupted B subunit pentamer formation and/or B subunit to GM1 receptor binding and that DEA interfered with organization of plasma membrane microdomains.

The abbreviations used herein have the following meanings (abbreviations not shown here have their meanings as commonly used unless specifically stated otherwise):

| Abbreviation | Full Name |
|---|---|
| ATP | adenosine triphosphate |
| DEA | diethyl azelate |
| M-CSF | macrophage colony-stimulating factor |
| G-CSF | granulocyte colony-stimulating factor |
| GM-CSF | granulocyte macrophage colony-stimulating factor |
| IL | interleukin |
| iNOS | inducible nitric oxide synthase |
| NOD | nucleotide oligomerization domain |
| PBS | phosphate buffered saline |
| PBMC | peripheral blood mononuclear cells |
| PGE2 | prostaglandin E2 |
| PRR | pattern recognition receptor |
| TLR | Toll-like receptor |

What is claimed is:

1. A method of inducing a localized analgesic effect in a subject suffering from pain selected from the group consisting of acute pain, chronic pain, nociceptive pain, neuropathic pain, nociplastic pain, traumatic pain, chemical pain, burn pain, ischemic pain, insect bite pain, prickling pain, musculoskeletal pain, rheumatoid or osteoarthritis pain, post-surgical pain, bone pain, and skin-related pain, the method comprising topically administering to the subject a composition comprising from about 20% to about 100% by weight of a therapeutically effective amount of diethyl azelate.

2. The method of claim 1, wherein inducing the localized analgesic effect is accomplished by disrupting a lipid raft of the subject by the dicarboxylic acid ester.

3. The method of claim 2, wherein the lipid raft comprises monosialotetrahexosylganglioside1 (GM1).

4. The method of claim 2, wherein the lipid raft comprises phospholipase D2 (PLD2).

5. The method of claim 2, wherein the disrupting of the lipid raft membrane results from the increase of the plasma membrane fluidity.

6. The method of claim 1, wherein inducing the localized analgesic effect, thereby inhibiting pain in the subject, comprises activating one or more receptors selected from the group consisting of pattern recognition receptors (PRR), nucleotide oligomerization domain (NOD) receptors, and Dectin receptors.

7. The method of claim 1, wherein inducing the analgesic effect, thereby inhibiting pain in the subject, comprises promoting the synthesis or release of the activity and/or expression of one or more of leptin, macrophage colony-stimulating factor (M-CSF), granulocyte colony-stimulating factor (G-CSF), granulocyte macrophage colony-stimulating factor (GM-CSF).

8. The method of claim 1, wherein inducing the localized analgesic effect, thereby inhibiting pain in the subject, comprises inhibiting the synthesis or release of the activity and/or expression of at least one of adenosine triphosphate (ATP), inducible nitric oxide synthase (iNOS) and prostaglandin E2 (PGE2).

9. The method of claim 1, wherein the administering is performed at about every 4 to about 8 hours.

10. The method of claim 1, wherein the administering is for a duration of from 1 day to 30 days.

11. The method of claim 1, wherein the subject is a human.

\* \* \* \* \*